(12) United States Patent
Teppke

(10) Patent No.: US 9,279,745 B2
(45) Date of Patent: Mar. 8, 2016

(54) MICROTOME

(71) Applicant: MICROM International GmbH, Walldorf (DE)

(72) Inventor: Dieter Teppke, Schwetzingen (DE)

(73) Assignee: MICROM International GmbH, Dreieich (DE)

( * ) Notice: Subject to any disclaimer, the term of this patent is extended or adjusted under 35 U.S.C. 154(b) by 108 days.

(21) Appl. No.: 14/237,351

(22) PCT Filed: Dec. 6, 2012

(86) PCT No.: PCT/EP2012/005043
§ 371 (c)(1),
(2) Date: Feb. 6, 2014

(87) PCT Pub. No.: WO2013/091786
PCT Pub. Date: Jun. 27, 2013

(65) Prior Publication Data
US 2014/0190324 A1  Jul. 10, 2014

(30) Foreign Application Priority Data
Dec. 19, 2011 (DE) .......................... 10 2011 121 366

(51) Int. Cl.
*G01N 1/06* (2006.01)
(52) U.S. Cl.
CPC ............... *G01N 1/06* (2013.01); *Y10S 83/9155* (2013.01); *Y10T 83/207* (2015.04)
(58) Field of Classification Search
CPC ......................... Y10S 83/9155; Y10T 83/207
USPC ........................................ 83/915.5, 167, 171
See application file for complete search history.

(56) References Cited

U.S. PATENT DOCUMENTS

| 3,227,020 | A | * | 1/1966 | Zeytoonian ..................... 83/162 |
| 3,649,108 | A | * | 3/1972 | Ahrens et al. ................... 352/84 |
| 4,700,600 | A | | 10/1987 | Pickett |
| 5,099,735 | A | * | 3/1992 | Kempe et al. .............. 83/699.61 |
| 5,740,708 | A | | 4/1998 | Tabone |
| 5,851,213 | A | * | 12/1998 | Berleth et al. ................ 606/167 |
| 5,960,640 | A | * | 10/1999 | Teppke ........................... 62/320 |
| 6,644,162 | B1 | * | 11/2003 | Temple et al. .................. 83/703 |
| 2007/0005357 | A1 | | 1/2007 | Moran |
| 2009/0181457 | A1 | | 7/2009 | Schmitt |
| 2009/0199716 | A1 | | 8/2009 | Schmitt |
| 2010/0043612 | A1 | * | 2/2010 | Ichiyanagi et al. ............. 83/105 |

FOREIGN PATENT DOCUMENTS

| DE | 1 748 387 | 7/1957 |
| DE | 25 06 255 | 9/1976 |
| DE | 89 10 373 | 11/1989 |
| DE | 694 02 197 | 9/1997 |
| DE | 198 24 024 | 12/1999 |
| DE | 692 29 133 | 1/2000 |
| DE | 10 2008 000 035 | 7/2009 |
| DE | 20 2010 011 369 | 12/2010 |
| EP | 1 094 310 | 4/2001 |
| JP | 2007187603 | 7/2007 |

* cited by examiner

Primary Examiner — Laura M Lee
(74) Attorney, Agent, or Firm — Paul Vincent

(57) ABSTRACT

A microtome has a blade holder on which a blade is mounted, an anti-roll device for supporting a section preparation that has been produced by means of the blade, and a suction device by means of which the section preparation can be picked up by suction and carried off. The suction device has a nozzle, with an adjustably mounted nozzle body, and a suction channel. Provision is made that the anti-roll device is mounted on the nozzle body and is adjustable, in particular pivotable, together therewith.

11 Claims, 2 Drawing Sheets

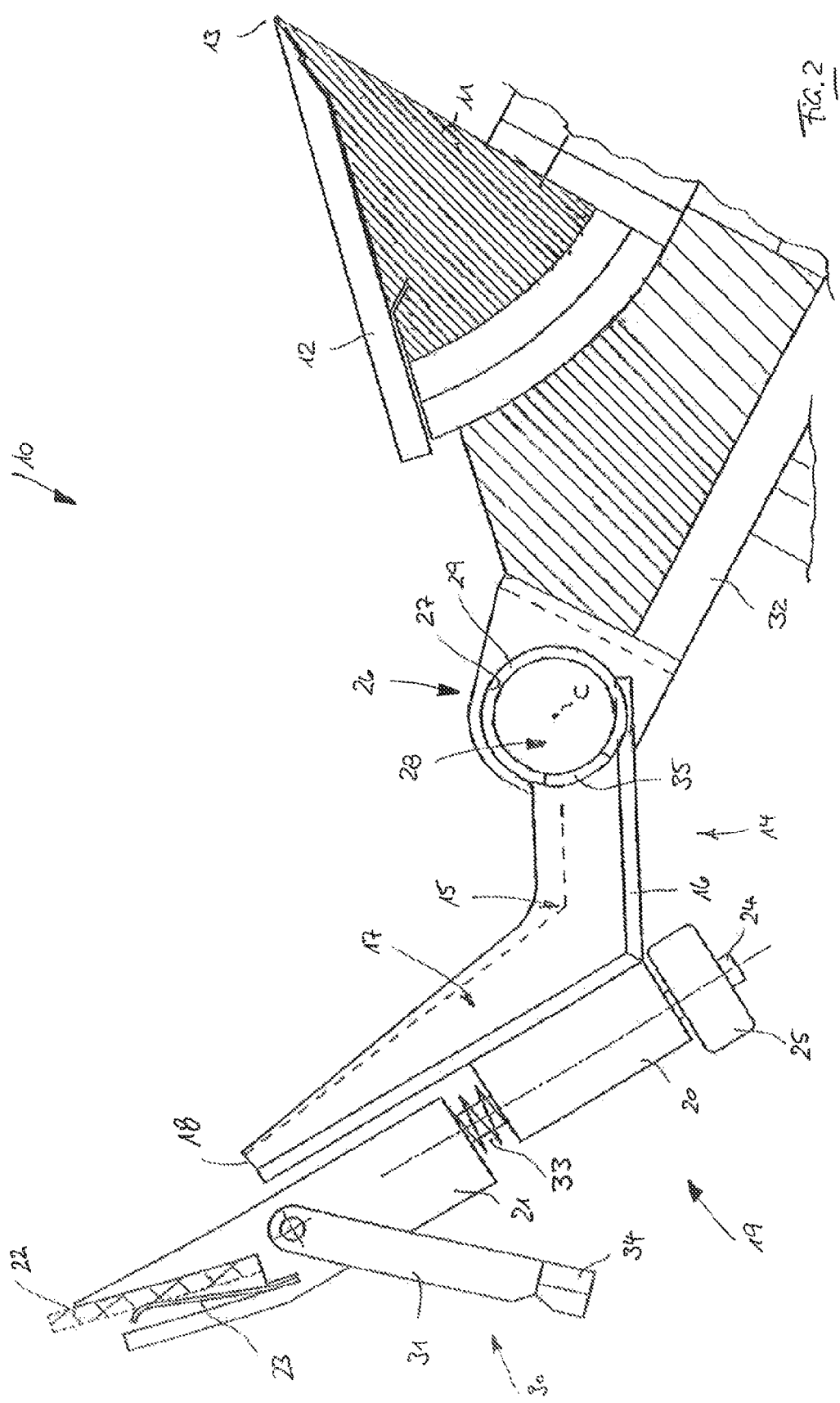

MICROTOME

This application is the national stage of PCT/EP2012/005043 filed on Dec. 6, 2012 and also claims Paris Convention priority from DE 10 2011 121 366.3 filed Dec. 19, 2011.

BACKGROUND OF THE INVENTION

The invention relates to a microtome, comprising a blade holder on which a blade is mounted, an anti-roll device for supporting a section preparation that has been produced by means of the blade, and a suction device by means of which the section preparation can be picked up by suction and carried off, wherein the suction device has a nozzle with an adjustably mounted nozzle body and with a suction channel.

A microtome is a cutting appliance with which very thin section preparations from a body, for example biological tissue, can be cut off for subsequent examination. In addition to the uses in medicine and biology, microtomes are also used for the examination of plastics.

A section preparation usually has a thickness of $10^{-4}$ m to $10^{-7}$ m. On account of this small thickness, the section preparations have a tendency to deform during the cutting process and in particular to form waves or even curls. To prevent this, or at least make it more difficult, an anti-roll device is known which is usually arranged above the blade and, with the latter, forms a slit-shaped passage through which the section preparation is guided, during which process the section preparation is subjected to a slight force intended to stabilize it in terms of its shape. A suitable anti-roll device is known in various designs.

Should the section preparation have deformed despite the use of an anti-roll device, it is then usually no longer suitable for the subsequent examination and has to be carried off and disposed of. For this purpose, it is known to use a suction device comprising a nozzle, with an adjustably mounted nozzle body, and a suction channel via which the nozzle is connected to a vacuum source. The nozzle body and therefore the nozzle are mounted adjustably and can be brought to a suction position, in which a nozzle opening is arranged close to the blade in order to pick up an unusable section preparation by suction. In addition, the suction force that can be generated by the suction device can also be used to support the anti-roll function. For cleaning purposes, it is possible to bring the nozzle body to a non-operational position, in which the nozzle is easily accessible for cleaning.

The anti-roll device is also mounted on an adjustable carrier and can be adjusted between an operational position, in which it acts on the section preparation together with the blade, and a non-operational position, in which the anti-roll device can be cleaned.

Since the installation space available for the adjustable mounting of the anti-roll device on the one hand and of the nozzle body on the other hand is greatly limited, the adjustable mounting of these two structural units is complicated in terms of design and unfavourable in terms of cost.

The object of the invention is to make available a microtome of said type in which an adjustment of the nozzle body and of the anti-roll device is effected in a manner that is simple in terms of design.

SUMMARY OF THE INVENTION

According to the invention, this object is achieved by a microtome having the features of the independent claim. Provision is thereby made that the anti-roll device is mounted on the nozzle body and is adjustable together therewith.

The invention proceeds from the principle that, instead of the anti-roll device and the nozzle body each being provided with its own dedicated adjustment device, the anti-roll device is mounted on the nozzle body directly or indirectly. Since the nozzle body is mounted so as to be adjustable, in particular pivotable about a pivot bearing, the anti-roll device is also adjusted and distanced from the blade when the nozzle body is adjusted. In this way, only one common adjustment device is needed, as a result of which the structural design is made simpler. In addition, the installation space, which is very limited in the case of a microtome, can be better utilized.

In a preferred embodiment of the invention, provision is made that the nozzle body is mounted pivotably on a pivot bearing together with the anti-roll device. In a development of the invention, provision can be made that the suction channel extends through the pivot bearing, as a result of which only a small installation space is needed for the suction channel.

The pivot bearing can have a recess, for example in the form of a circular cylindrical bore, into which a tube part of circular cylindrical cross section is inserted rotatably, preferably with a tight fit. The nozzle body can be held on the tube part and can pivot with the latter in the recess bore.

The nozzle has a suction opening, which is arranged close to the blade, in particular offset with respect to the cutting edge thereof, and forms the mouth of the suction channel. The suction channel can be arranged at least in part in the nozzle body and can be in flow communication with the interior of the tube part, in particular via a passage in the wall of the tube part. A vacuum can be generated in the bore or the recess by means of a vacuum generator, which vacuum is then also effective in the interior of the tube part, and in the area of the suction channel formed in the nozzle body, and therefore at the suction opening of the nozzle body.

To be able to easily clean the nozzle body and the anti-roll device, provision can be made, in a development of the invention, that the tube part is removable from the recess. Thus, the tube part can be removed with the nozzle body and with the anti-roll device and cleaned at a cleaning station. The removal of the tube part from the recess is performed in a simple way, by means of the tube part being pulled in its longitudinal direction out of the recess and, after cleaning, being pushed back into the recess. Removal of the tube part with the nozzle body and with the anti-roll device is also useful if the user, during the cutting process, requires direct access to the section preparation, in which case said structural parts would be in the way. Handling is thus made easier.

In a preferred embodiment of the invention, provision is made that the anti-roll device is arranged on that side of the nozzle body directed away from the blade. When the anti-roll device is located in its operational position, it is arranged just above the cutting edge of the blade. The nozzle body with its suction opening is then located between the blade and the anti-roll device so as to reliably ensure that an unusable section preparation can, if necessary, be picked up by suction.

When the microtome is not in use, the blade has to be covered to avoid injury. For this purpose, it is known to place a shoe-shaped or sleeve-shaped cover, a so-called finger guard, on the blade. To start operating the microtome, the finger guard firstly has to be removed, which poses the risk of its being lost, since it is a loose separate part. According to the invention, provision can be made that the finger guard is mounted adjustably on the anti-roll device. The user can adjust the finger guard between a protection position, in which it at least partially covers the blade and protects the user, and a release position, in which the blade lies exposed and can cut the desired section preparation. The adjustment of the finger guard can be effected by a linear or curved adjustment movement, provision preferably being made that the finger guard is mounted pivotably on the anti-roll device.

The finger guard can be a pivotable bow which, on the one hand, has a high degree of stability and, on the other hand, can safely cover the blade. In a development of the invention, the finger guard can have a grip part, by which the user can take hold of the finger guard, and therefore the anti-roll device and the nozzle body, and pivot it away from the blade about the pivot bearing and pull it out of the pivot bearing.

Further details and features of the invention will become clear from the following description of an illustrative embodiment and by reference to the drawing, in which:

BRIEF DESCRIPTION OF THE DRAWING

FIG. 2 shows a view corresponding to FIG. 1, with the nozzle body in a pivoted position.

DESCRIPTION OF THE PREFERRED EMBODIMENT

Figure 1:
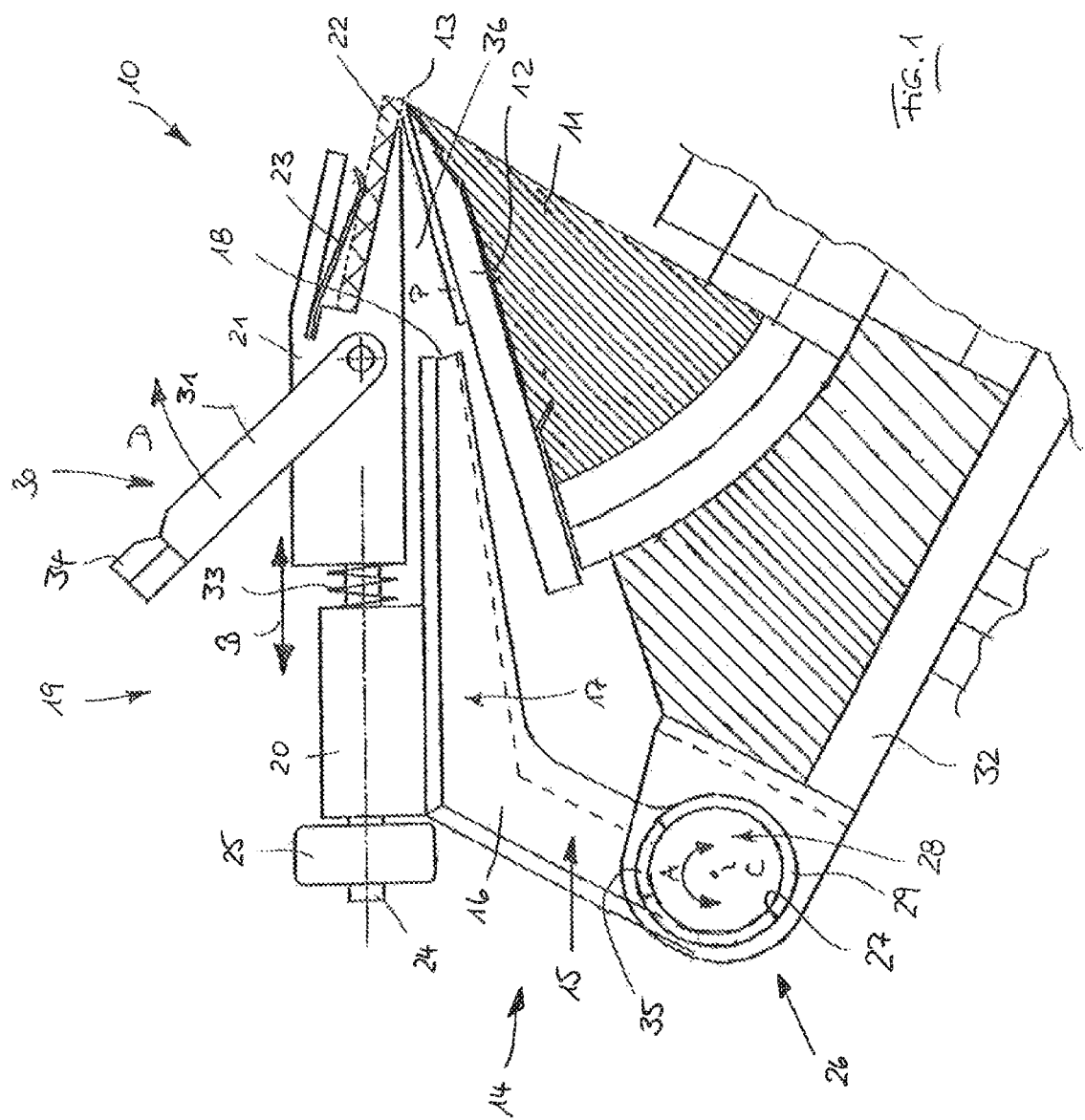
FIG. 1 shows a schematic, partially cut-away side view of the component parts of a microtome that are essential to the invention.

A microtome 10 shown in FIGS. 1 and 2 has a machine-fixed bearing part 32 on which a blade holder 11, carrying a blade 12 with a cutting edge 13, is mounted adjustably in a conventional manner.

A recess 27 in the shape of a bore is formed on the bearing part 32, is connected to a vacuum source (not shown) and is part of a suction device 14. A tube part 29 of circular cross section for forming a pivot bearing 26 is inserted with a tight fit into the recess 27, such that the tube part 29 can be turned or pivoted in the recess 27 about a pivot axis C, as is indicated by the double arrow A. The tube part 29 is sealed off at its front end on the outside, such that the vacuum is also effective in an interior 28 of the tube part 29.

The tube part 29 is connected to a suction nozzle 15. The suction nozzle 15 comprises a nozzle body 16 with, on the inside, a suction channel 17 which, at one end thereof, communicates with the interior 28 of the tube part 29 via a passage 35 and, at the opposite end, opens out at a suction opening 18 arranged close above the blade 12 and offset with respect to the cutting edge 13 of the latter.

On that side of the nozzle body 16 directed away from the blade 12, an anti-roll device 19 is secured on said nozzle body. This anti-roll device has a main part 20 which is connected rigidly to the nozzle body 16 and on which a holding part 21 is mounted displaceably by means of a guide pin 24, as is indicated by the double arrow B. Between the main part 20 and the holding part 21, a spring 33 is arranged which secures the position of the holding part 21 relative to the main part 20. The adjustment of the holding part 21 relative to the main part 20 is effected in a customary way by means of a setting wheel 25.

At its front end directed toward the blade 12 or the cutting edge 13 of the latter, the holding part 21 has a clamp 23, with which a so-called anti-roll glass 22 is exchangeably mounted. The anti-roll glass 22 is oriented in such a way that its front end forms, with the cutting edge 13 of the blade 12, a narrow gap through which a section preparation P, cut off by the blade 12, can be acted upon on its upper face and can be stretched.

Between the underside of the holding part 21, or the anti-roll glass 22, and the top face of the blade 12, a slit-shaped space 36 is formed in which the suction opening 18 of the nozzle body 16 opens.

A so-called finger guard 30, formed by a pivotably mounted bow 31, is provided on the holding part 21.

FIG. 1 shows the bow 31 in its non-operational position, in which it is pivoted rearwards. From this position, it can be pivoted in the direction of the arrow D, such that it lies over and covers the cutting edge 13 of the blade 12 and possibly also the front end of the anti-roll glass 22 arranged immediately above the latter.

In addition, a grip part 34 is formed on the bow 31. This allows a user to take hold of the bow 31 by the grip part 34 and pivot it into its operational position in which it covers the cutting edge 13. The suction device 14 and the anti-roll device 19 are pivotable as a structural unit about the pivot axis C of the pivot bearing 26. The user can carry out this pivoting movement by taking hold of said structural unit via the grip part 34 and pivoting it about the pivot axis C to the position shown in FIG. 2. In this position, the blade lies completely free and can be easily cleaned. The structural unit composed of the suction device 14 and of the anti-roll device 19 can be released from the bearing part 32 by pulling the tube part 29 from the recess in the longitudinal direction, i.e. the direction perpendicular to the drawing plane. The thereby fully released and independent structural unit can then be easily cleaned and, after cleaning, can be correspondingly used again.

I claim:

1. A microtome having a blade for producing a section preparation, the microtome comprising:
   a bearing part;
   a blade holder to which the blade is mounted, said blade holder being mounted to said bearing part for adjustment relative thereto;
   a suction device, said suction device structured to suction and carry off the section preparation, said suction device having a nozzle with an adjustably mounted nozzle body, said suction device defining a suction channel, wherein said nozzle body is pivotally mounted to said bearing part for pivoting relative to said bearing part and relative to said blade holder; and
   an anti-roll device for supporting the section preparation produced by the blade, wherein said anti-roll device is mounted on said nozzle body and is adjustable together therewith.

2. The microtome of claim 1, wherein said nozzle body is mounted pivotably on a pivot bearing.

3. The microtome of claim 2, wherein said suction channel extends through said pivot bearing.

4. The microtome of claim 2, wherein said pivot bearing has a recess and a tube part inserted rotatably into said recess.

5. The microtome of claim 4, wherein said nozzle body is held on said tube part.

6. The microtome of claim 5, wherein a portion of said suction channel is formed in said nozzle body and is in flow communication with an interior of said tube part.

7. The microtome of claim 4, wherein said tube part is removable from said recess.

8. The microtome of claim 1, wherein said anti-roll device is arranged on a side of said nozzle body directed away from said blade.

9. The microtome of claim 1, further comprising an adjustable finger guard mounted on said anti-roll device.

10. The microtome of claim 9, wherein said finger guard is formed by a pivotable bow.

11. The microtome of claim 9, wherein said finger guard has a grip part.

* * * * *